United States Patent [19]

Degler, Jr. et al.

[11] 4,228,800
[45] Oct. 21, 1980

[54] BIPOLAR ELECTROSURGICAL KNIFE

[75] Inventors: Howard E. Degler, Jr., St. Petersburg; David E. Clark, Gainesville; John J. Hren, Gainesville; David A. Jenkins, Gainesville; Paul F. Johnson, III, Gainesville, all of Fla.

[73] Assignee: Concept, Inc., Clearwater, Fla.

[21] Appl. No.: 893,422

[22] Filed: Apr. 4, 1978

Related U.S. Application Data

[63] Continuation of Ser. No. 695,649, Jun. 14, 1976, abandoned.

[51] Int. Cl.³ .............................................. A61B 17/39
[52] U.S. Cl. ............................ 128/303.14; 128/303.17
[58] Field of Search ...................... 128/303.13–303.18, 128/40 J, 800

[56] References Cited

U.S. PATENT DOCUMENTS

| | | | |
|---|---|---|---|
| 1,735,271 | 11/1929 | Groff | 128/303.14 |
| 2,012,316 | 8/1935 | Miles | 128/303.14 X |
| 2,126,070 | 8/1938 | Wappler | 128/303.17 X |
| 3,234,356 | 2/1966 | Babb | 128/303.14 X |
| 3,532,095 | 10/1970 | Miller | 128/303.13 |
| 3,699,967 | 10/1972 | Anderson | 128/303.14 |
| 3,768,482 | 10/1973 | Shaw | 128/303.14 X |
| 3,901,242 | 8/1975 | Storz | 128/303.15 |
| 3,987,795 | 10/1976 | Morrison | 128/303.14 |
| 4,161,950 | 7/1979 | Doss et al. | 128/303.14 |

FOREIGN PATENT DOCUMENTS

| | | | |
|---|---|---|---|
| 564168 | 10/1958 | Canada | 128/303.14 |
| 2428886 | 1/1976 | Fed. Rep. of Germany | 128/303.14 |
| 243478 | 7/1946 | Switzerland | 128/303.18 |

*Primary Examiner*—Lee S. Cohen
*Attorney, Agent, or Firm*—Gipple & Hale

[57] ABSTRACT

An electrosurgical instrument comprising a handle which holds a blade assembly comprising a plurality of electrodes and insulation members positioned between the electrodes.

The blade assembly comprises a center electrode of specified thickness, insulation members secured to the center electrode and a plurality of side electrodes secured to the insulation members. The center electrode and insulation members are cut to form a cutting edge having a composite angle of less than 120° thus allowing easier electrosurgical performance.

The electrodes are connected inside the nonconductive handle to a circuit whose output consists of a high frequency electrical current which forms a circuit through tissue intervening between and in contact with the electrodes when the instrument is used.

17 Claims, 12 Drawing Figures

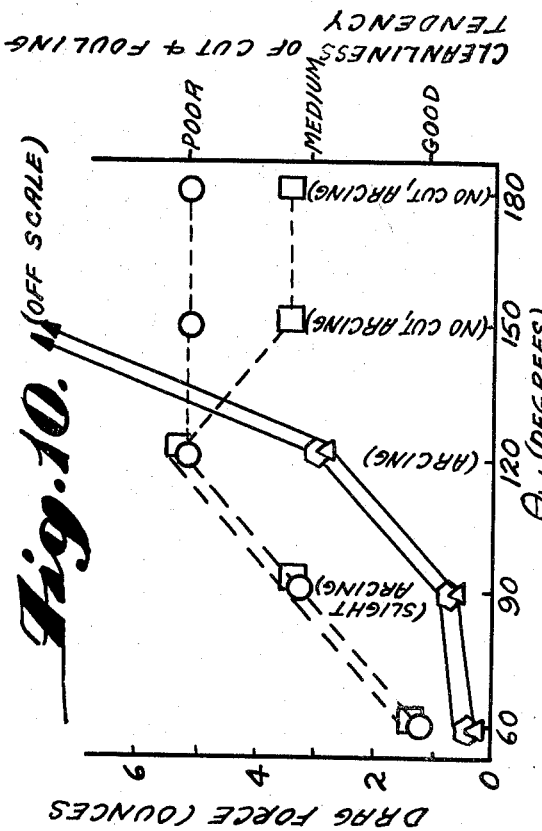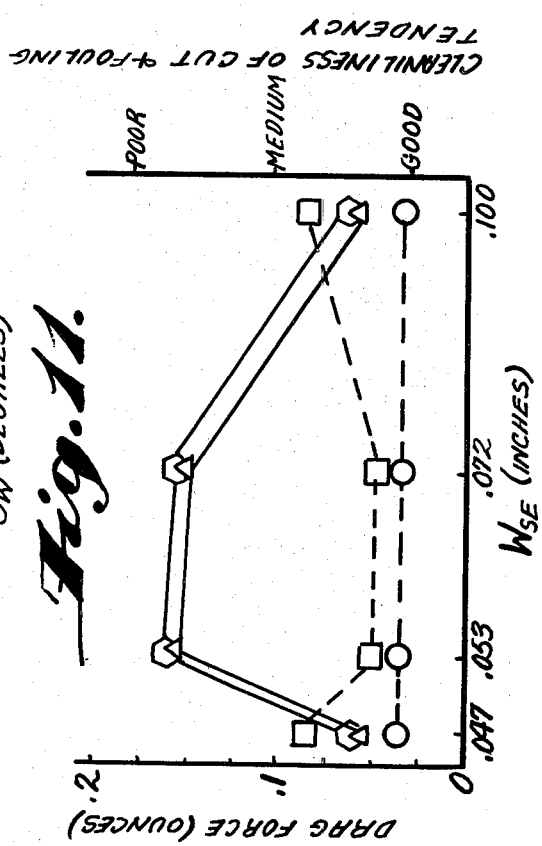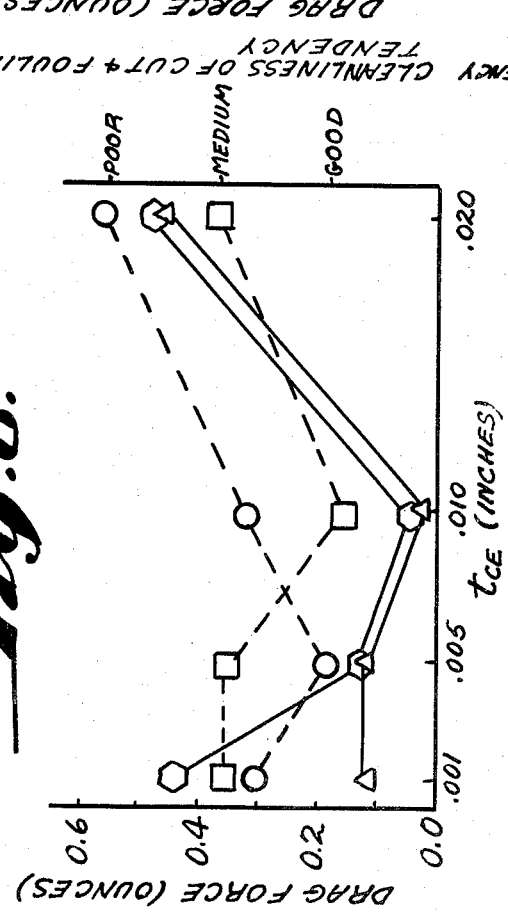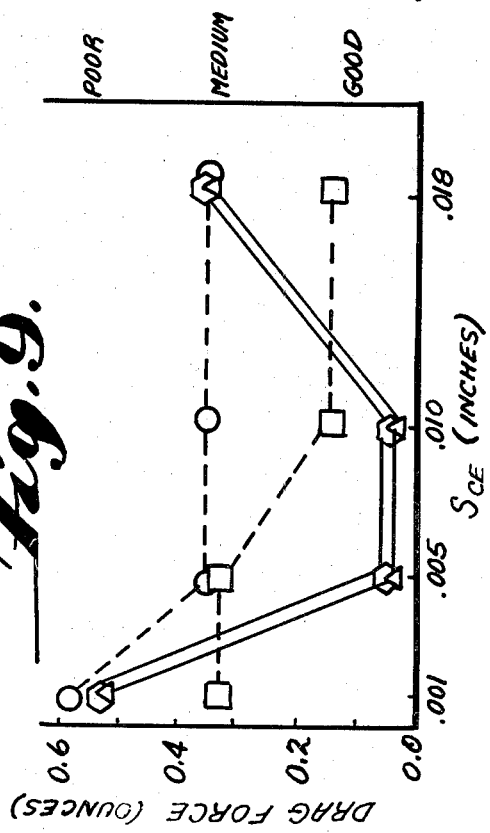

BIPOLAR ELECTROSURGICAL KNIFE

This is a continuation, of application Ser. No. 695,649 filed June 14, 1976 now abandoned.

FIELD OF INVENTION

This invention relates in general to surgical instruments and more particularly to a sterilized bi-polar electrosurgical instrument capable of selectively cutting tissue and/or coagulating blood. Additionally, a novel configuration and composition of the electrosurgical blade tip is described.

DESCRIPTION OF THE PRIOR ART

It is well known in the art to use electrical surgical apparatus of the monopolar type in which an active electrode is used in connection with a metal ground plate on which a patient is positioned. This apparatus forms a complete circuit so that various cutting or coagulating procedures can be accomplished. Such an electrosurgical device is shown in U.S. Pat. No. 3,601,126. Electrosurgical units of this type may be hazardous in that they require a ground or return plate to minimize the patient to ground impedance and to complete the radio frequency circuit. Units requiring such a ground plate may not only hinder the operator and present a physchological deterent to a patient but also subject the patient to the possibility of a radio frequency burn when non-uniform contact is made between the ground plate and the patient's skin. Various other electrosurgical instruments utilize a hand held surgical instrument which can be operated from separate power supplies so that the tip of the instrument is provided with either a cutting energization or a coagulating energization. Patents which show the use of such surgical instruments are U.S. Pat. Nos. 3,875,945 and 3,699,967.

Various attempts have been made to develop electrosurgical instruments which do not have a monopolar arrangement or are not provided with hot resistance tips. Such developments have taken the form of bi-polar and multipolar surgical instruments. One such bi-polar instrument is shown by U.S. Pat. No. 166,184. In this patent an electrode is disclosed with a solid nonconducting head into which the end of electrode wires are imbedded so that they are insulated from each other. Another U.S. Pat. No. 1,814,791 discloses a bi-polar coagulating instrument in which electrodes are partially imbedded in the lateral surface of an insulated tip a uniform distance apart so that an output circuit is completed through the tissue intervening between and in contact with the electrodes. A third U.S. Pat. No. 1,983,669 discloses a bi-polar coagulating device in which two twisted wires are separated from one another by lamination of an insulatory material. A multipolar instrument is shown by U.S. Pat. No. 3,460,539 wherein a surgical instrument is described which has a plurality of exposed conducting rods circumferentially placed in the body of the insulating material for cauterization.

The present invention provides a unitary bi-polar electrosurgical device that can be used for either cutting or coagulating procedures when used in conjunction with a proper electrosurgical generator. The tissue in the proximal area surrounding the blade is used to close the circuit between the insulated electrodes on the blade.

SUMMARY OF INVENTION

The present invention discloses a disposable hand held electrosurgical cutting and coagulating device in which the type of cutting or coagulating current desired is selected by the setting of a switch which activates the proper circuitry thus transferring the desired mode of current to the novel electrode configuration forming the blade of the surgical instrument. Thus the instrument can perform selected electrosurgical functions without the weed of utilizing separate cutting tips or different instruments.

The instrument uses a novel blade assembly comprising a center electrode, insulation members secured to the electrode and side electrodes secured to the insulation members. The blade components form a critically angled cutting edge and the thickness of the center electrode in combination with the side electrodes decrease drag force and allows cleaner incisions.

Performance of the present bi-polar blade as compared with a monopolar blade exhibit the following general chaiacteristics: (1) cutting is preformed at a much lower power than with a monopolar blade; (2) at identical power settings and cutting speeds, the bi-polar blade leaves a cleaner incision than the monopolar blade; (3) no ground plate is required for the bi-polar blade; (4) starting and shallow cuts seem to be somewhat more difficult with the bi-polar blade, although automatic tests revealed no peaking in the drag force at the start of a cut; (5) both monopolar and bi-polar blades become fouled with burned tissue fairly quickly; however, operating at lower power settings, the deposit which forms on bi-polar blades can be wiped off easily without excessive scrubbing; and (6) when desired, electro-coagulation of the tissue between the electrodes is readily accomplished.

Thus it is seen that the bi-polar blade produces far less burning of the adjacent tissue as the cut is made, while experiencing less drag force.

The monopolar blade is at full potential at the leading edge, where cutting occurs, and also along the sides, where only additional burning of the tissue takes place. The center electrode of the bi-polar blade is considerably more active than the side electrodes, and thus cutting power is concentrated where it is needed.

The foregoing advantages of this invention will be more readily apparent and appreciated as the same becomes better understood from the following detailed description of the preferred embodiment of the invention when taken in conjunction with the accompanying drawings in which:

BRIEF DESCRIPTION OF THE DRAWINGS

FIG. 8 is a graph charting stable cutting drag, starting drag, cleanliness of cut and fouling tendency in relation to the thickness of a tantalum center electrode used in the blade assembly;

FIG. 9 is a graph charting stable cutting drag, starting drag, cleanliness of cut and fouling tendency in relation to the thickness of a stainless steel center electride used in the blade assembly;

FIG. 10 is a graph charting stable cutting drag, starting drag, cleanliness of cut and fouling tendency in relation to the wedge angle of the blade assembly;

FIG. 11 is a graph charting stable cutting drag, starting drag, cleanliness of cut, and fouling tendency in relation to the side electrode width of the blade assembly.

DETAILED DESCRIPTION OF THE DRAWINGS

Figure 1:
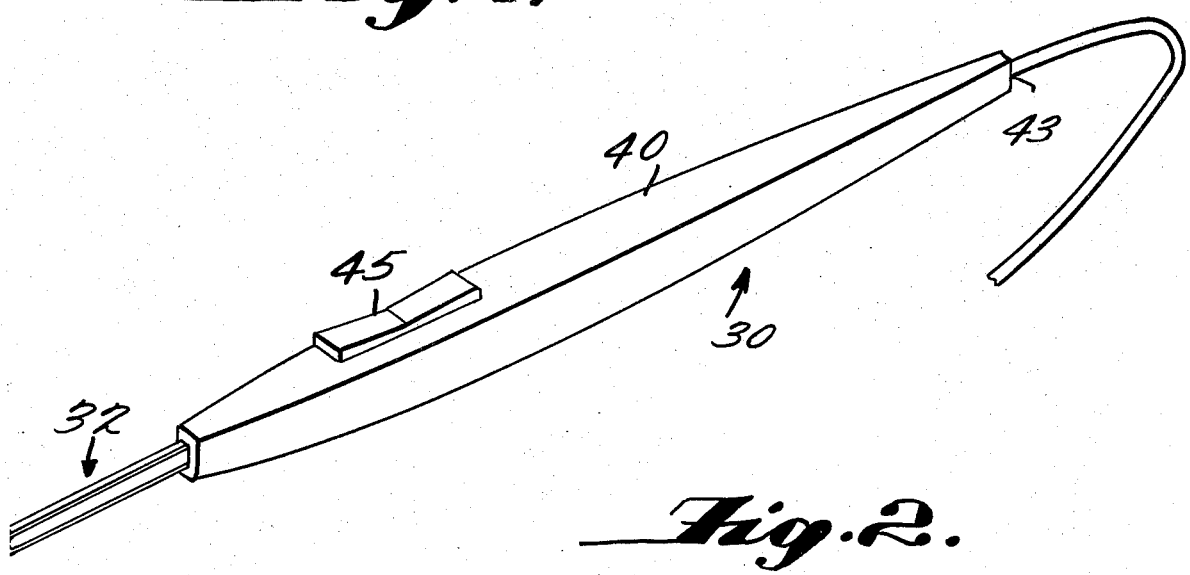
FIG. 1 is a perspective view of the electrosurgical instrument.
Figure 3:
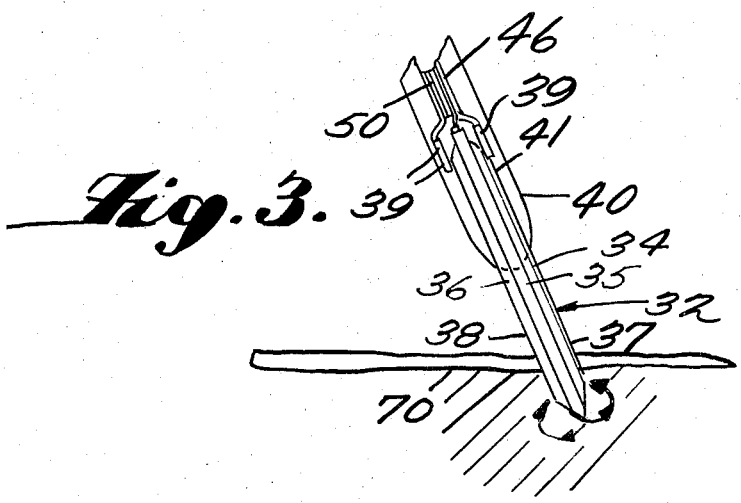
FIG. 3 is an enlarged side schematic view partially in section of the tip of the instrument in FIG. 2 illustrating the currents passing from one conductor to the other through the tissue.
Figure 6:
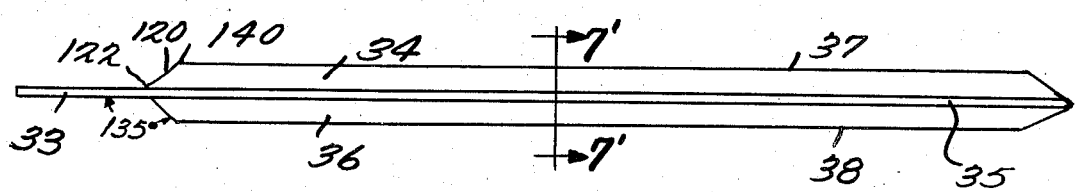
FIG. 6 is a side elevational view of the electro-surgical blade shown in FIG. 5.

A cutting and coagulating electrosurgical instrument 30 is shown in FIG. 1. In the preferred embodiment of the invention as shown in FIGS. 1, 3 and 6, the bi-polar blade assembly 32 comprises a center electrode 35, insulation members 34 and 36 secured to the center electrode and outer electrodes 37 and 38 secured to insulation members 34 and 36 respectively. The distal end 33 of the blade assembly is mounted in a blade seat formed in the non-conducting handle casing 40.

Figure 2:
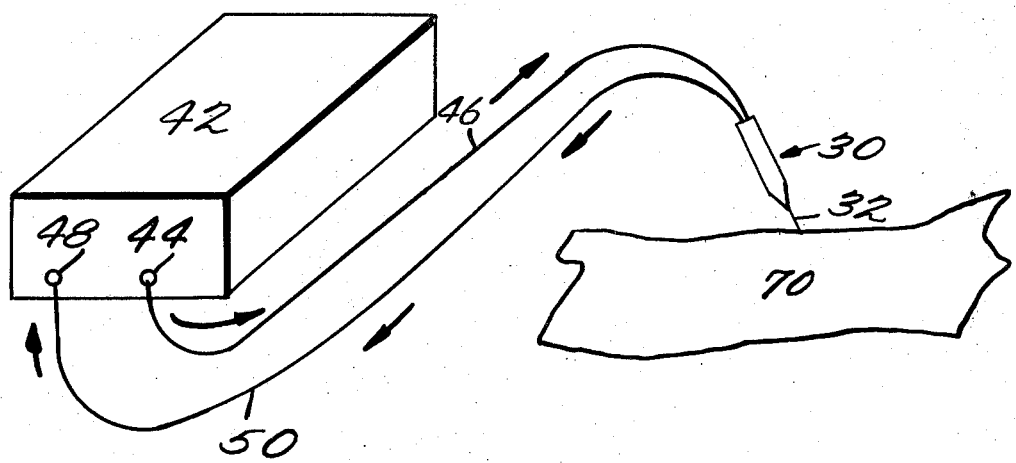
FIG. 2 is a schematic view of the instrument shown in FIG. 1 connected with an electrical wave form generator.
Figure 4:
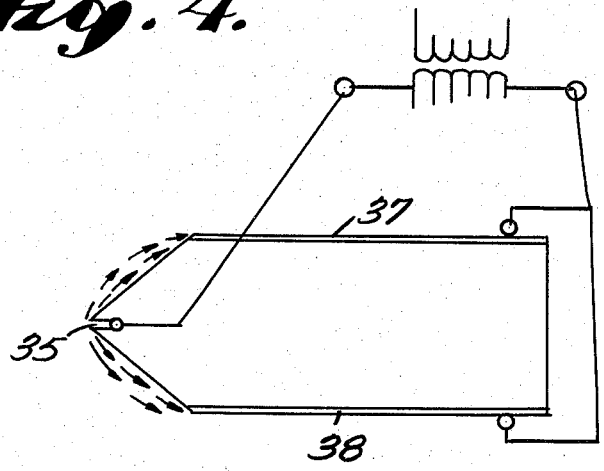
FIG. 4 is a schematic cross-sectional view of the blade geometry.

As shown in FIGS. 1-3, the handle casing 40 is provided with contacts 39 which are secured to the casing and positioned adjacent the blade seat 41 which facilitate the electrical connection of the blade electrodes 35, 37 and 38 to the electrosurgical generator 42. As shown in FIG. 4 the side electrodes 37 and 38 are shorted together within the handpiece and act as electrical return electrodes during the cutting operation. Flexible insulated wires sufficient in length to allow the surgeon unrestricted movement are run through a bore 43 cut through the casing to provide the electrical connection between the contacts and the electrosurgical generator.

The handle 40 is preferably pencil shaped so that it fits the contours of the hand and is shown with a three-way selector switch 45. The three-way selector switch allows the operator to select the desired mode of wave form emanating from the electrosurgical generator 42. In this manner, the instrument can be used for solely cutting or coagulating or for a combination of the two functions. Middle electrode member 35 is connected to an active isolated output 44 of the electrosurgical generator 42 through its associated contact and insulated connector wire 46 and side electrodes 37 and 38 are connected to a patient output 48, which is electrically isolated from ground of the electrosurgical generator 42 through its associated contact and insulated connector wire 50.

Figure 12:
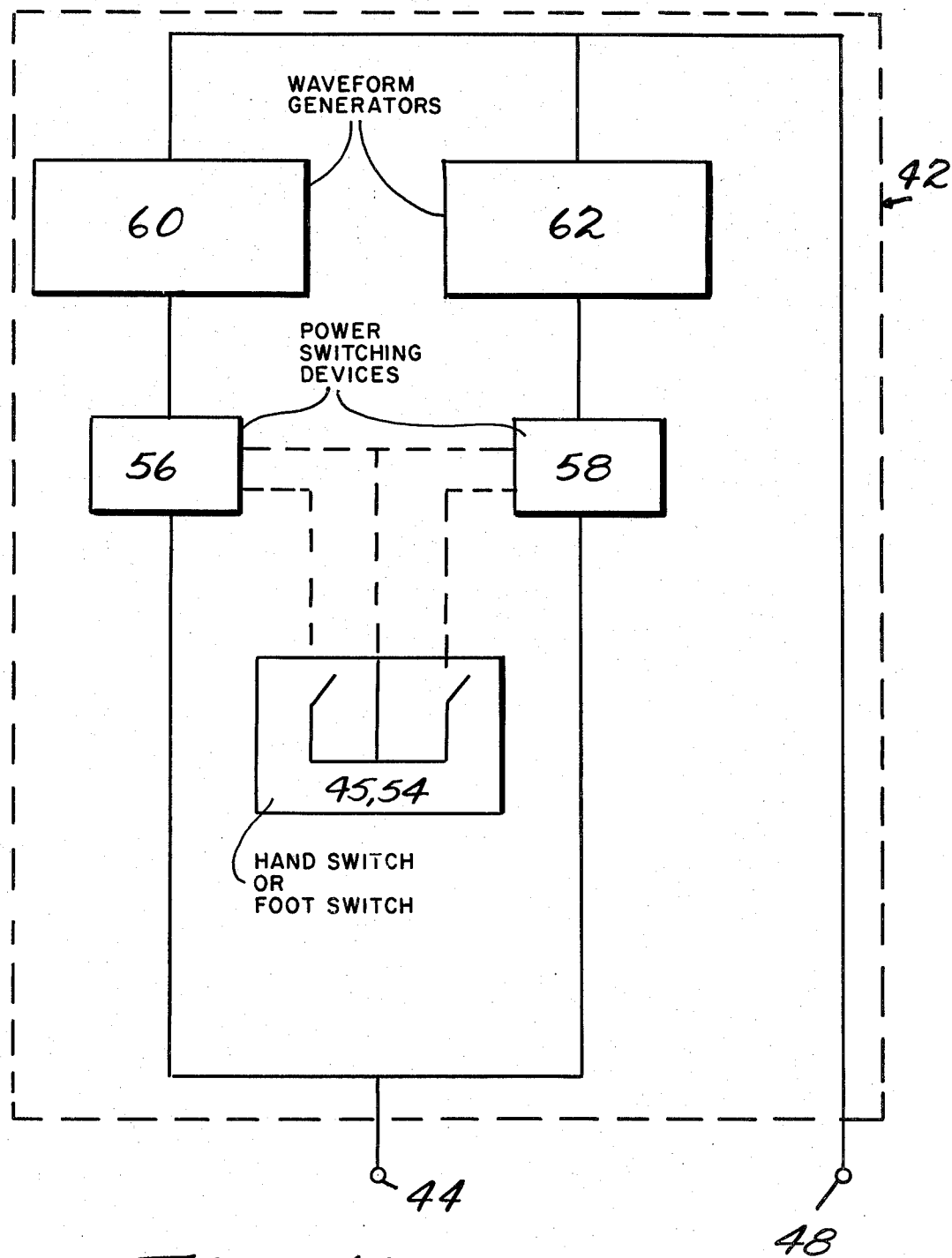
FIG. 12 is an electric schematic of the electrosurgical generator and switching circuitry.

FIG. 12 of the invention discloses a hand switch 45 or a foot switch 54 selectively connected to power switching devices 56 and 58 so that radio frequency electrical energy for cutting or coagulating wave forms can be passed into output 44 of the electrosurgical generator. Power switching device 56 when activated by the hand switch 45 serves to complete the circuitry schematically shown as block 60. This circuitry 60 is well known in the art to generate cutting forms. Another power switching device 58 as adapted to complete the circuitry schematically shown by block 62 to generate coagulation wave forms which are also well known in the art. The arrows shown in FIGS. 2-4 denote direction of current flow.

In regard to the various types of wave forms generated, this application specifically incorporates by reference U.S. Pat. Nos. 3,699,967 and 3,875,945. Thus the invention can use a decaying sinusoidal current for the coagulation current or a continuous sinusoidal current for the cutting current at a frequency different than the resonant frequency of the coagulation current. Thus it can be seen that the coagulation current is generated at one frequency and the cutting current at another frequency.

Additional wave forms can be obtained by providing the electrosurgical tip with a radio frequency voltage which in unmodulated for operation in the cutting mode or modulated for operation in the coagulating mode.

Either one of the respective wave forms can be generated through output 44 into the electrosurgical instrument balde. As previously indicated such circuits are well known in the art and are described in previous patents mentioned in the prior art in this invention.

The construction of the blade allows for the emission and collection of radio frequency electrical energy in a proximal area causing either cutting or coagulating action depending on the wave form used when the ratio frequency electrical energy bridges the gap across the conductors through the tissue 70. When the electrosurgical instrument is activated by switch 45, current passes from output 44 through connection wire 46 in either the cutting or coagulating wave form mode to conductor 35 and passes through the skin or the tissue 70 of the patient to conductors 37 and 38 completing the circuit.

Figure 5:
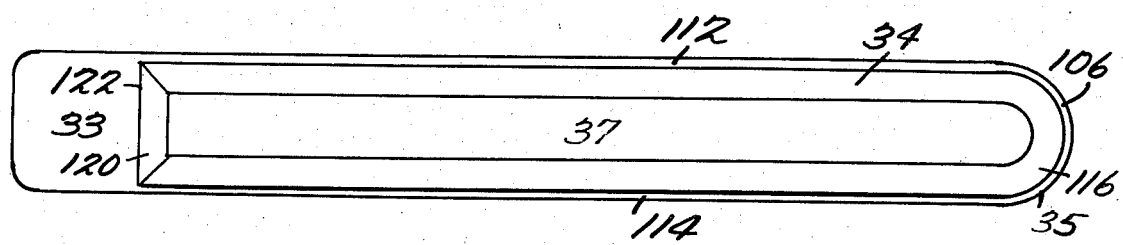
FIG. 5 is a top plan view of the electrosurgical blade.
Figure 7:
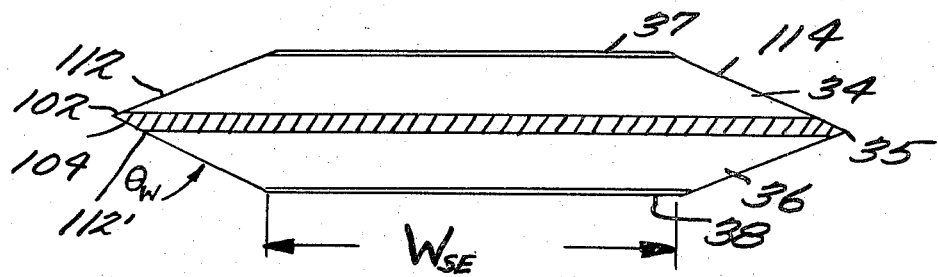
FIG. 7 is an enlarged cross-sectional view taken along line 7'-7' of FIG. 6.

FIGS. 5-7 show the preferred geometrical configuration of the electrosurgical blade. As viewed from the top, the blade has a symmetrical "sandwich" configuration with the middle electrode 35 being surrounded by insulator members 34 and 36. On the opposite sides of the insulator members are the metallized side electrodes 37 and 38. The center electrode 35 has beveled edges 102 and 104 on its top and bottom surfaces which form an angular cutting surface around the electrode body. A semicircular tip 106 is formed on the front end of the electrode for cutting purposes while the rear of the electrode forms the center electrode contact tab 33. When the blade is inserted into the handle 40, the center electrode contact tab 33 is fitted into the blade seat of the instrument and is connected directly to insulated connector wire 46.

The insulation members 36 and 34 evidence a trapazoidal configuration when viewed from the top. The insulation members 34 and 36 are both identical in shape. Insulation member 34 is comprised of two flat beveled sides 112 and 114 and a shorter beveled end 120 and a circular beveled tip 116. The tip 106 of the center electrode extends further out than the semi-circular tip 116 of the insulation member. In this manner a small center electrode tip area is exposed. The beveled side edges 102 and 104 of the center electrode also extend beyond the beveled sides 112 and 114 of the insulator to provide a cutting edge around the blade. The rear wall 120 of the insulation member connects the side walls 112 and 114 at the rear while circular tip 116 connects them at the tip. The rear wall 120 is also beveled with respect to the center electrode 35. As can be readily seen by FIG. 5 the rear wall 120 of the insulator has its lower edge 122 adjacent to the center electrode surface at the center electrode contact tab 33. The angle formed by the adjacent beveled surfaces of the two insulation members and the center electrode is in the preferred embodiment 60°. This angle $\theta w$ formed between the adjacent beveled side of walls 112 and 112' of the two insulation members and center electrode, is a critical angle which will be later discussed. The angle is constant along the side walls of the insulation members and the tip portion 116. As best seen in FIGS. 5-7, the center electrode also is comprised of two beveled surfaces 102 and 104 which form the same critical angle.

The side or outer electrodes 37 and 38 are thin sheets of a metallized substance. The side electrodes are bounded by the upper edge 140 of the rear wall 120, side walls 112, 114 and bevelled semi-circular tip 116 of the insulation member 34. The insulation members 34 and 36 are bonded to the center electrode 35 by high temperature commercially available epoxy.

The three electrode blade design, shown schematically in FIG. 4 is a practical solution to the "starting" problem occurring when the blade is first used to provide an initial incision. The three electrode design substantially eliminates the high drag force occurring at the beginning of a cut by limiting the area of the center electrode in a contact with the body tissue. Due to the fact that the AC output of the power supply is fully isolated, the electrode making best contact with the tissue remains nearly at the potential of the tissue, and is thus inactive. The limited area of the center electrode results in its being active continuously, consequently allowing successful starts. As also indicated in FIG. 4, the side electrodes 37 and 38, which tend to be inactive, are shorted together within the handpiece and act as the return electrode during cutting. The bi-polar blade, when compared to the monopolar blade produces less burning of the adjacent tissue as the cut is made and experiences less drag force. The drag force is the amount of resistance a portion of body tissue will exhibit to cutting with a specific bi-polar or monopolar electrosurgical blade.

FIG. 8 is a graph illustrating the increase in drag force as a function of the thickness of the center electrode ($t_{ce}$) for a tantalum center electrode. Two drag forces are indicated, i.e. stable cutting drag and starting drag. It can be seen that good results are obtained when the thickness of the center electrode is in the range of 0.005 to 0.015 inches. The preferred embodiment contemplates the center electrode thickness as 0.010 inches. Similar results are shown in FIG. 9 wherein the drag force is plotted as a function of the center electrode thickness for a stainless steel center electrode.

FIG. 10 is a graphical illustration of the drag force (measured in ounces) as a function of the critical angle ($\theta_w$) measured in degrees on a blade with a tantalum center electrode. The critical angle is the angle formed between the walls of the center electrode and walls of the insulation members. As can be seen the lower drag forces occur when the critical angle is 120° or less. In the preferred embodiment the critical angle is constructed at 60°.

FIG. 11 is a graphical illustration of the drag force (measured in ounces) as a function of the width (in inches) of the side electrodes. As can be readily seen good results are obtained in the range about 0.047 inches to 0.100 inches. In the preferred embodiment, the preferred width of the side electrode is 0.062 inches.

FIGS. 8-11 also illustrate the plotting of the cleanliness of cut and the electrode's fouling tendency as a function of various critical parameters, i.e. the thickness of the center electrode, the critical wedge angle and the width of the side electrodes. These factors were also utilized in determining the optimum physical parameters of the blade.

Inherent in the three electrode design is a relatively high current density located at the center electrode. Center electrodes composed of a highly refractory metal, e.g. molybdenum, perform adequately whereas less refractory material, e.g. gold platinum, tends to melt in use. The material for the center conductor must be both reasonably refractory and medically acceptable. Requirements for the materials used in the side electrodes are far less stringent.

A substantial amount of work has been done in neural tissue, since it is quite delicate and represents a "worst case" model. Orthopedic appliances research has also been responsible for much of the information available on the toxicity of implanted materials. Research in this area involves both hard and soft tissues, especially bone, tendon, cartilage and muscle. A great deal of work has been performed involving endiothelial tissue cultures because of the necessity for a material which can provide variable feed-through between the physiological and the external environment.

These studies indicate that certain materials are toxic to animal tissue while other materials are non-toxic and therefore medically acceptable. Material selected from those non-toxic materials can be used for the center electrodes for bi-polar cutting blades if the required physical material requirements are met. Another consideration in the choice of materials is the fact that the tissue immediately adjacent to the incision made with an electrosurgery blade is destroyed. Thus, this tissue may be replaced by non-functional scar tissue. The effects of small amounts of metal or ceramic in fibrous scar tissue should be negligible. Non-toxic materials, which have been considered in the present invention and are medically acceptable for the present electrosurgical application, include tantalum, molybdenum, nickel, aluminum, nichrome, selected stainless steels, iridium, $Al_2O_3$, $SiO_2$ and most glasses.

In the preferred embodiment either tantalum or stainless steel are employed as the material composition for the center electrode. In the preferred embodiment of the blade the insulator members are comprised of $Al_2O_3$ (99 plus percent pure). The high purity $Al_2O_3$ insulators and indeed other insulators are necessary to avoid breakdown of the blades initiated by arcing. The preferred embodiment utilizes metallized silver as the composition of the side electrodes. The side electrodes operate at a much lower potential than the center electrode and so may be of a less refractory metal that is relatively easy to apply. Since insignificant amounts of the side electrodes will be deposited along the incision, a material such as silver, while not suitable for implants because of its long term corrosion behavior, does not present a histological problem.

The method of assembly of the blades, i.e. bonding the insulation members onto the center electrode with commercially available Ecco Bond 104, cured at 400° F., provides a dramatic increase in bending strength. Differential thermal contraction of the metal center electrode during cooling results in a residual compressive stress in the $Al_2O_3$ members sides, a condition analogous to that found in pre-stressed concrete beams.

While the preferred embodiment of the invention has been disclosed, it is understood that the invention is not limited to such an embodiment since it may be otherwise embodied in the scope of the appended claims.

What is claimed is:

1. A bipolar electrosurgical instrument comprising an electrically insulated housing, constructed of a nonconductive material and having a substantially pencil shaped configuration, a blade assembly mounted in said housing and projecting from said housing, said blade assembly comprising a center electrode, insulation means on opposite sides of said electrode and side electrodes ranging in width from 0.047 inches to 0.100 inches secured to said insulation means so that they are symmetrically disposed with respect to said center electrode and separated from said center electrode by said insulation means, said blade assembly center electrode being formed with a substantially rectangular linear shape with linearly oriented beveled edges and connected to said insulation means, said insulation means comprising two insulator members of substantially rectangular linear shape positioned on each side of said center electrode with aligned beveled edges, said two insulator members being composed of at least 99% pure $Al_2O_3$, a source of energy, means for connecting said electrodes to said source of energy so that an output circuit of the source of energy comprising a high frequency electrical current is completed through tissue intervening between and in contact with said electrodes, said side electrodes being shorted together within said housing and acting as return electrodes during operation of this instrument and switch means connected to said source of energy for selectively energizing said electrodes.

2. A surgical instrument as claimed in claim 1 wherein said center electrode is tantalum and said side electrodes are silver.

3. A surgical instrument as claimed in claim 1 wherein said center electrode is stainless steel and said side electrodes are silver.

4. A surgical instrument as claimed in claim 1 wherein said center electrode has a beveled cutting edge forming a 60° angle.

5. A surgical instrument as claimed in claim 1 wherein said center electrode has a thickness ranging from 0.005 to 0.015 inches.

6. A surgical instrument as claimed in claim 1 wherein said center electrode has a thickness of substantially 0.010 inches.

7. A surgical instrument as claimed in claim 1 wherein said center electrode and insulator members edge form a blade assembly edge having a wedge angle which is not greater than 120°.

8. A surgical instrument as claimed in claim 1 wherein said center electrode and insulator members edges form a blade assembly cutting edge having a wedge angle of substantially 60°.

9. A surgical instrument as claimed in claim 1 wherein said two insulator members are bonded to said center electrode on opposite sides of said center electrode to form a residual compressive stress in the $Al_2O_3$ insulator members.

10. A surgical instrument as claimed in claim 9 wherein said bonding is with a high temperature epoxy.

11. A bipolar electrosurgical instrument comprising an insulated handle, and blade assembly mounted in said handle and projecting from said handle, said blade assembly comprising a linearly shaped, center electrode body ranging from 0.005 to 0.015 inches in thickness, platelike insulation members composed of at least 99% pure $Al_2O_3$ secured to opposite sides of said center electrode and outer electrodes of silver composition secured to said insulation members in symmetrical relationship to said center electrode and separated from said center electrode by said insulation members, said center electrode and insulation members being beveled to form a blade assembly with proximal and distal ends having an edge wedge angle which does not exceed 120° with the center electrode extending past the insulation members at the distal end and edges of the blade assembly, a source of energy, means for connecting said electrodes to said source of energy so that an output circuit of said source of energy comprising a high frequency electrical current is completed and maintained through tissue intervening between and in contact with said electrodes, said source of energy comprising means to selectively generate wave forms to said electrodes and switch means adapted to select said wave forms for transmission into said electrodes for performance of the desired electrosurgical function.

12. A surgical instrument as claimed in claim 11 wherein said center electrode is tantalum and said insulation members are $Al_2O_3$.

13. A surgical instrument as claimed in claim 11 wherein said center electrode is stainless steel and insulation members are $Al_2O_3$.

14. A bipolar electrosurgical instrument comprising an insulated handle, and blade assembly mounted in said handle and projecting from said handle, said blade assembly comprising a linearly shaped center electrode body about 0.010 inches in thickness with a beveled edge, insulation members having a composition of $Al_2O_3$ of at least 99% purity bonded to opposite sides of said center electrode with a high temperature epoxy and outer electrodes secured to said insulation members and separated by said insulation members from said center electrode, said electrodes and insulation members forming a blade assembly in which the edges of the insulation members are beveled and cooperate with the center electrode beveled edge to form an angle of about 60°, a source of energy, means for connecting said electrodes to said source of energy so that an output circuit of the source of energy comprising a high frequency electrical current is completed through tissue intervening between and in contact with said electrodes, said source of energy comprising means to generate cutting wave forms to said electrodes and switch means adapted to selectively transmit said wave forms into said electrodes for performance of the desired electrosurgical function.

15. A surgical instrument as claimed in claim 14 wherein said outer electrodes are about 0.062 inches in width.

16. A bipolar blade assembly suitable for use with a bipolar electrosurgical instrument comprising a linearly shaped center electrode body with a substantially semicircular distal end ranging about 0.010 inches in thickness with a beveled edge, two identical insulation members of lesser length and width than said center electrode formed with an insulator material of about 99% pure $Al_2O_3$ composition, said insulation members presenting a substantially trapezoidal cross-section configuration and defining beveled edges, said insulation members being secured to opposite sides of said center electrode leaving a center electrode tip area exposed and beveled side edges of the center electrode exposed and outer electrodes of lesser length and width than said center electrode secured to said insulation members and separated from said center electrode by said insulation members, said outer electrodes being symmetrically disposed with respect to said center electrode and formed with a width ranging from 0.047 to 0.10 inches, said center electrode and insulation members forming a blade wedge angle of about 60°, a source of energy, means for connecting said electrodes to said source of energy so that an output circuit of the source of energy comprising a high frequency electrical current is completed through tissue intervening between and in contact with said electrodes, said source of energy comprising means to generate cutting wave forms to said electrodes and switch means adapted to selectively transmit said wave forms into said electrodes for performance of the desired electrosurgical function.

17. A blade assembly as claimed in claim 16 wherein said center electrode is tantalum and said outer electrodes are silver with said center electrode, insulation members and outer electrodes being bonded together with a high temperature epoxy.

* * * * *